United States Patent [19]

Moulds

[11] Patent Number: 5,175,083
[45] Date of Patent: Dec. 29, 1992

[54] IMMUNOASSAY FOR THE QUANTITATION OF HUMAN C4 GENE PRODUCTS

[75] Inventor: Joann M. Moulds, Houston, Tex.

[73] Assignee: Board of Regents, University of Texas, Austin, Tex.

[21] Appl. No.: 384,714

[22] Filed: Jul. 24, 1989

[51] Int. Cl.$^5$ .......................................... G01N 33/573
[52] U.S. Cl. ..................................... 435/7.4; 436/501; 436/507; 436/518; 436/821; 435/975
[58] Field of Search ................ 435/7.1, 7.8, 7.9, 7.92, 435/7.94, 965, 968, 7.4, 975; 436/501, 507, 506, 518, 821

[56] References Cited

PUBLICATIONS

Antes et al., J. Immunol. Melthods 102:149–156, 1987.
Maggio, Ed., *Enzyme Immunoassay*. CRC Press, Boca Raton, Fla., 1980. pp. 167–179.
Campbell et al.; *Biochem. J.* 189:67–80 (1980).
Spinella et al.; *Complement* 1:187–193 (1984).
O'Neill; *Vox Sang.* 47:362–365 (1984).
Giles and Ford; *Transfusion* 26(4):370–374.
Holme et al.; *Immunogenetics* 27:295–297 (1988).
Giles et al.; *Immunogenetics* 26:309–312 (1987).
Larsson and Sjöquist; *J. Clin. Lab. Immunol.* 27:39–43 (1988).
Larsson and Sjöquist; *J. Immunol. Methods* 119:103–109 (1989).

Primary Examiner—Esther L. Kepplinger
Assistant Examiner—Donna C. Wortman

[57] ABSTRACT

Utilizing mouse monoclonal antibodies which recognize Rodgers 1 and Chido 1 epitopes carried on the C4A and C4B molecules, and heat aggregated IgG to activate C1, an immunoassay was developed for the quantitation of complement components, including total C4, C4A and C4B. Interassay variation was 12.4%, 11.5% and 10.8%, respectively. The immunoassay was compared to the quantitation of total C4 by radial immunodiffusion by testing 103 random white controls and gave a Pearson's product moment correlation coefficient of 0.81. Three genetic total C4 deficient individuals were nonreactive in all three assays. This activated assay is specific, reproducible and superior to existing methods for the quantitation of C4A and C4B and detection of the heterozygous C4 null states.

18 Claims, 2 Drawing Sheets

| DONOR # | C4 ALLOTYPE | RODGERS TYPE | CHIDO TYPE | C4A mg/dl | cv % | C4B mg/dl | cv % | C4d mg/dl | cv % |
|---|---|---|---|---|---|---|---|---|---|
| 1 | A3, B1 | Rg 1,2 | Ch1,2,3,4,5,6 | 12.6 | 11.3 | 13.7 | 10.8 | 21.4 | 10.3 |
| 2 | A2, B1 | Rg 1,2 | Ch1,2,3,4,5,6 | 8.6 | 12.7 | 9.6 | 7.9 | 17.0 | 11.4 |
| 3 | A1, A4, B2 | Rg 1,2 | Ch1-2,3,4-5,6 | 9.7 | 8.2 | 15.4 | 9.3 | 20.4 | 7.5 |
| 4 | A3, AQ0, B1 | Rg 1,2 | Ch1,2,3,4,5,6 | 8.1 | 10.9 | 24.1 | 15.0 | 26.6 | 18.8 |
| 5 | AQ0, B1 | Rg-1-2 | Ch1,2,3,4,5,6 | 0 | 0 | * | * | 27.6 | 6.5 |
| 6 | A3, B1, BQ0 | Rg 1,2 | Ch1,2,3,4,5,6 | 22.1 | 12.3 | 10.8 | 11.0 | 27.4 | 20.3 |
| 7 | A3, BQ0 | Rg 1,2 | Ch NEGATIVE | * | * | 0 | 0 | 30.9 | 7.8 |
| 8 | A3, BQ0 | Rg 1,2 | Ch NEGATIVE | 17.9 | 13.4 | 0 | 0 | 16.8 | 16.2 |
| MEAN VARIATION | | | | | 11.5 | | 10.8 | | 12.4 |

FIG.-2

LEGEND: * SAMPLE USED FOR STANDARD CURVE

IMMUNOASSAY FOR THE QUANTITATION OF HUMAN C4 GENE PRODUCTS

FIELD OF THE INVENTION

The present invention relates generally to assays for complement components and more specifically to a novel, accurate, and sensitive solid phase assay for C4. The assay can be used to detect total C4 as well as relative proportions of C4 isotypes in the serum of an individual and in C4 allotyping studies.

DESCRIPTION OF THE RELATED ART

Assays of the complement system proteins provide valuable clinical information regarding the severity and duration of an immune complex-mediated process, especially in autoimmune diseases such as systemic lupus erythematosus (SLE). The fourth component of complement (C4) is of particular interest in this respect as C4 levels SLE have been correlated with increased disease activity and worsening of the patient's clinical manifestations. (1, 2).

The fourth component of human complement (C4) is a glycoprotein of about 200-kDa molecular weight. Hepatocytes and macrophages synthesize C4 as a single chain protein of 1722 amino-acids called pro-C4 that is subsequently cleaved to produce a structure of three polypeptide chains (alpha, beta, and gamma) linked by disulfide bonds. When this molecule comes into contact with activated C1 (the first complement component), it is cleaved into two subunits, C4a, a low molecular weight (about 5,000M) fragment of the alpha chain, and C4b, (the remainder of the molecule) which functions together with C1 in carrying out subsequent steps in the activation cascade. See reference 35 for a more complete review of the complement activation cascade.

C4 is encoded by two genes located within the major histocompatibility complex (MHC). Two C4 isotypes are produced (C4A and C4B) which exhibit biochemical, antigenic, and functional differences that have been localized to a fragment of the C4b subunit, C4d. C4A is more acidic, migrates faster in agarose gel electrophoresis, binds preferentially to amino groups in vitro, is less hemolytically active against sensitized sheep erythrocytes, and is more efficient in precipitating immune complexes than C4B (3).

Besides the two major isotypes of C4, over 13 allotypes of C4A and 22 allotypes of C4B have been identified on the basis of differences in electrophoretic mobility (4). Most of the C4A proteins carry the Rodgers (Rg) blood group antigens while C4B proteins carry Chido (Ch) antigens. Rare exceptions have been noted; C4A1 usually carries Ch1 1 and not Rg1, and some C4B5 allotypes carry Rg1 but lack Ch determinants (5, 6). These serologic specificities have been defined using polyclonal antisera, usually from multiparous females or multiply transfused individuals. Monoclonal antibodies have been produced to several of the same determinants detected by polyclonal antisera (7-9).

The controlling mechanisms for the production of C4 are not well understood. Some studies (10-12) indicate that the amount of total C4 produced depends on the number of functional C4 genes, i.e., those individuals with absent or silent alleles of C4A (C4A*Q0) or C4B (C4B*Q0) have lower total C4 levels. Uko et al. (13) have suggested that normal ranges should be established based on the number of null alleles present. This may be of particular importance in patients with systemic lupus erythematosus (SLE) where a high frequency of C4A exists due largely to a C4A,21-OHA gene deletion (14) inherited with the MHC haplotype HLA-A1,B8,DR3. In order to accomplish this goal, however, a sensitive and reliable assay for measurement of C4 levels is required.

Total serum C4 can be measured by immunochemical techniques involving specific antigen-antibody interaction and functional hemolytic assays. Functional assays are reportedly 1000 to 10,000 times more sensitive than immunochemical tests (15) but are time consuming, difficult to perform, and cannot be used to differentiate the various allotypes present in a sample.

Estimation of C4A and C4B levels has been accomplished by visual inspection or densitometric scanning of C4 allotyping gels or crossed immunoelectrophoresis gels (16). Even using modified techniques (17), i.e., carboxypeptidase, these methods are semi-quantitative and poorly standardized. While scanning densitometry is more precise than visual interpretation, it has not substantially improved the detection of C4 null alleles (18). It may be difficult to determine heterozygous C4 nulls in samples exhibiting overlapping bands. Indeed, in the 102 Caucasians studied in this manner by Uko et al. (12), the number of C4 null alleles could only be assigned in 74 individuals.

Analysis by restriction fragment length polymorphism (RFLP) may detect C4 gene deletions, duplications or gene conversions (3, 19, 20) all of which may result in an apparent C4 null status at the protein level. This assay is far from satisfactory, however, because the mere presence of C4 genes does not ensure that an individual will make C4 protein. The failure of certain individuals to express normal levels of C4 may be caused by nonfunctional (silent) alleles and errors in transcription or post-translational processing of C4.

Recently, Holmes et al. (21) described an ELISA for the quantitation of C4A and C4B. This assay requires goat anti-C4 for capture and employs a complicated sandwich of mouse anti-human C4, rabbit anti-mouse IgG, and donkey anti-rabbit antisera. The assay is time-consuming, difficult to optimize, and prone to interference by anti-species antibodies. Additional disadvantages are the failure of the goat antisera to bind all available C4 and the poor correlation between results obtained using this assay and results obtained with other assays for C4 (nephelometry and radial immunodiffusion).

Therefore, a convenient, rapid, sensitive, reproducible, and accurate assay for measurement of C4 was greatly needed and sought after by those of skill in the art.

SUMMARY OF THE INVENTION

The present inventor has discovered an assay that overcomes the problems of the type set forth above. This novel assay provides a rapid, sensitive, accurate and convenient method of measuring total C4 as well as C4A and C4B levels in serum or other fluids. Aggregated immunoglobulin bound to a solid matrix has been discovered to be surprisingly effective when employed as a reagent for capture and assay of C4. When activated by aggregated immunoglobulin, the proteolytic C1 complex cleaves native C4 and covalently binds the C4d fragment. Antibodies that recognize epitopes on the C4d fragment are added to the captured C4 and the amount of C4, C4A or C4B present quantitated by measuring the amount of antibody bound.

In a broad and general sense the immunoassay comprises the steps of obtaining a preparation of aggregated immunoglobulin molecules, affixing the immunoglobulin to a solid matrix, exposing the immunoglobulin to a sample to be assayed for C4 under such conditions that the C4 will bind to the immunoglobulin, exposing the bound C4 to an antibody that has binding affinity for C4 under conditions such that binding between C4 and the antibody occurs; and measuring the amount of antibody bound.

Generally the immunoglobulin used for aggregation will comprise a preparation containing a relatively high proportion of IgG. However, IgM immunoglobulin can be also be used.

The antibodies capable of binding C4 may be either polyclonal or monoclonal. Antibodies directed against the Chido and Rodgers antigens are preferred as they enable one to obtain information concerning relative proportions of isotypes C4A and C4B as well as total C4 concentrations.

In a preferred embodiment, the antibody is coupled to an enzyme capable of cleaving a selected substrate to produce a chromophore and the amount of antibody bound to C4 is determined by adding the substrate so that it is cleaved by the enzyme to produce the chromophore and detecting the chromophore. In a related embodiment, the anti-C4 antibody is directly coupled to a labeling molecule and antibody bound to C4 is measured by detecting the label, for example, a fluorescent or radioactive label.

In yet other embodiments, a so called "indirect" labeling procedure is used. With those embodiments, the anti-C4 specific antibody, referred to herein as the "primary antibody", is not usually labeled. Instead, a labeled second reagent, referred to as the "secondary reagent," which is capable of specifically binding the primary antibody is added. The secondary reagent is usually an immunoglobulin that can be labeled in any of a number of ways, including all of those specifically set forth above. However, other molecules having affinity for the antibody, e.g., staphylococcal protein A, may also be used as secondary reagents. In addition, where the primary antibody is coupled to a small molecule, e.g., biotin, the secondary reagent may comprise a molecule, e.g., avidin, having binding specificity for the avidin. The system can be expanded further with tertiary reagents, etc., but this makes the assay more tedious to perform.

The assay may be packaged and sold in kit form. Therefore, the invention also includes a kit for detecting C4 which comprises a first container comprising aggregated immunoglobulin formulated for binding to a solid matrix, and a second container comprising an antibody capable of binding to C4. When the immunoglobulin is bound to the matrix and a test sample containing C4 is brought into contact with the matrix-bound immunoglobulin, the C4 binds to the immunoglobulin, and addition of the antibody from the second container results in binding of C4. With this kit, one can detect C4 by detecting the antibody bound to the C4.

In one embodiment, the first container of the kit may contain the aggregated immunoglobulin present, preferably in concentrated form, in a vial or tube from which it is removed and then added to the solid matrix. In an alternative embodiment, the first container may comprise the well or inner surface of a culture dish or other suitable solid matrix to which the immunoglobulin has been affixed.

Optionally, the kit may comprise an additional container comprising a selected, known, or reference concentration of C4. Such known or constant C4 preparations are useful as controls, for example, to generate standard curves.

In yet other embodiments the kit may comprise a container comprising C1.

Although any of the above mentioned labeling materials and techniques may be employed for use with the kit, in a preferred embodiment, the antibody is labeled with an enzyme capable of cleaving a substrate to produce a chromophore, and the kit further comprises a container comprising the substrate.

Although the examples relate specifically to detection of C4, in yet other embodiments, the assay or kit may be modified so as to allow detection of certain other complement components, for example C1, by using antisera or antibodies specific for C1 instead of antibodies directed against C4.

These and other aspects of the invention will become more apparent from a description of particular embodiments when read in conjunction with the drawings.

BRIEF DESCRIPTION OF THE DRAWING

FIG. 2. Selected donors for standardization of the activated immunoassay. Intra-assay coefficient of variation (cv) is based on 10 assays of each donor sample. Donors 4 and 5 had deleted C4A*Q0, 21-OH genes on Southern blot analysis; all others had intact genes.

DESCRIPTION OF A PREFERRED EMBODIMENT

Figure 1:
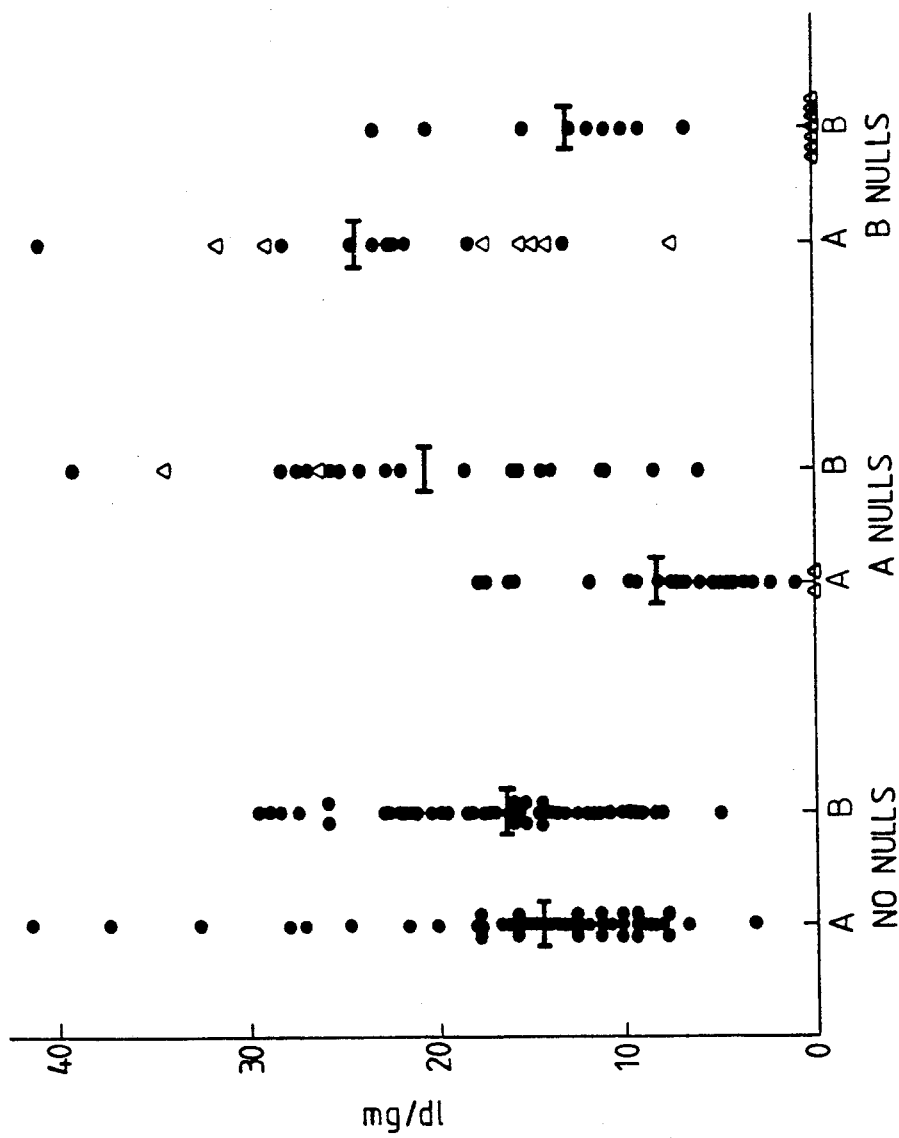
FIG. 1. Levels (mg/dl) of C4A and C4B by EIA in 103 Caucasian donors (58 male, 45 female). Subjects were divided into 3 groups based on C4A and C4B null alleles determined by allotyping. In individuals with one C4A*Q0, mean C4A levels were significantly lower than C4B (p.<001); in individuals with one C4B*Q0 mean C4B levels were lower than C4A (p.<001). In subjects with no null genes, while levels of C4A are lower than C4B, the differences were not statistically significant. Homozygous C4 null status is indicated by triangle.

The immunoassay of the present invention provides a convenient, simple, sensitive, and reproducible method to assay a test sample for the presence of total C4 levels. The assay also enables accurate and quantitative measurement of most C4 isotypes, as detected through the presence or absence of selected epitopes, most commonly those defined by the Chido (Ch) and Rodgers (Rg) antigens.

To practice the invention, one first obtains a preparation of immunoglobulin molecules, for example from the serum of a animal or individual. One of the outstanding advantages of the present invention is that immunoglobulin not possessing any particular antigenic specificity may be used. In fact, virtually any immunoglobulin capable of activating C1 when aggregated will suffice. However, where human immunoglobulin is used, purified immunoglobulin preparations containing a relatively high proportion of IgG3 and/or IgG1 are preferred for use with the present invention; immunoglobulin molecules belonging to these subclasses are better at activating C1 than are immunoglobulins of the IgG2 or IgG4 subclasses. Immunoglobulin molecules produced from myeloma or hybridoma cell lines may also be used successfully.

Preferably, the immunoglobulin will be aggregated by treatment with heat, for example, incubation at 60-65 degrees Centigrade for about 10 to 30 minutes. However, other modes of inducing aggregation, for example, ultrasonication, or chemical coupling may also be used successfully with the aid of the present disclosure.

The aggregated immunoglobulin is attached to a solid matrix, for example, the internal surface of a well of a plastic microtiter plate or culture dish. Most commonly this step will be performed by simply allowing the protein to adsorb to the plastic, although the immunoglobulin could also be attached in other ways—i.e., chemical coupling—if desired. Generally, if the simple adsorption technique is used, the aggregated immunoglobulin is allowed to adsorb to the plastic for a suitable period of time, commonly 1 hour at 37 degrees Centigrade or overnight at 4 degrees Centigrade. The plate is then treated or "blocked" with a second, usually inert, protein to prevent proteinaceous components of the sample to be tested or other reagents used in the assay from adsorbing to the plastic non-specifically. A number of suitable proteins for this purpose are known to those of skill in the art. Most commonly, commonly available and inexpensive proteins like albumin and casein are used but virtually any inert protein can be used. Although it is preferable to use the immunoglobulin coated matrix shortly after preparation, the prepared matrixes, e.g., immunoglobulin coated microtiter plates, can be stored for at least about one month, preferably in a moist environment at about 4 degrees Centigrade. Generally, the plates should not be frozen or allowed to dry out.

In most cases, the sample to be tested will comprise serum which may be obtained by standard techniques. For most purposes, use of serum is preferable to use of plasma since anticoagulants in the latter have been observed to interfere with the assay, presumably by inactivating C1 present in the sample. Generally, for example where serum is used, the sample should separated immediately and assayed or frozen (preferably at $-70$ degrees Centigrade) for future assay. Alternatively, the serum may be kept on ice or at 4 degrees Centigrade for about 4-6 hours prior to separation. Care should be taken to avoid heating of the sample as the complement components are heat labile.

Although serum is a preferred fluid for assay, the invention should not be considered to be so limited as it may be used to measure C4 levels in virtually any fluid preparation so long as care is taken not to denature or inactivate the active components in such fluid. Moreover, in some cases, use of other fluids will actually be preferred. For example, in patients with SLE, one may wish to measure the circulating C4d levels. Therefore, in those patients and in others in which it is desired to measure C4d levels, one may collect plasma using an anticoagulant (e.g. EDTA) that interferes with the activity of C1. Consequently, only C4 activated in vivo would bind to the aggregated immunoglobulin and be detected in the assay.

Preferably, prior to testing, the sample should be diluted in a suitable buffer, e.g., phosphate buffered saline, by at least about 1:25 to overcome the effects of possible C1 inhibitors present in the sample. Optionally, the buffer may contain additional "blocking" protein. An aliquot of the sample is brought into contact with the matrix-bound aggregated immunoglobulin and incubated under conditions which allow activation and binding of C1 to t he aggregated immunoglobulin and subsequently, activation and binding of C4 to the immunoglobulincomplex. Of course, for those, events to occur, the incubation conditions must be such that a source of C1 is present. Most conveniently, this C1 may be provided in the very test sample used to assay C4 levels, e.g., serum. However, in some cases it may prove desirable to add an additional source of C1 to the assay. If so, a suitable source is the purified C1 component obtained commercially, for example from Cytotech, San Diego, Calif.

In the experiments described below, the inventor found that incubation overnight at 4 degrees Centigrade was suitable and convenient. However, those of skill in the art may develop other incubation protocols, for example, incubation at 37 degrees for 1 hour, that may also prove entirely satisfactory.

After incubation, the solid matrix is generally washed to remove unbound serum and sample components. For this step, the inventor used a phosphate buffered saline solution containing 0.05% of a commercially available detergent, Tween 20 TM polyethylene-sorbiton, monolaurate. However, with the aid of the present disclosure, the washing buffer and conditions may be modified by those of skill in the art. For example, other detergents such as Brij TM polyoxyethyleneglyool aodecyl ether, Triton X TM octyphenoxy-polyethoxy-ethanol, Tween 80 TM polyoxyethylene-sorbitan mono-oleate, or Nonidet-P40 TM octyl phenol ethylene oxide, could be used in lieu of the Tween, or in some cases, the detergent can be omitted entirely. Of course, suitable buffers other than PBS could also be used. It is important that the buffer used not be one that will substantially destroy the antigenic epitopes of the C4 molecule, for example, by total denaturation of the protein.

After washing, the solid matrix to which the aggregated immunoglobulin and C4 (if present in the test sample) is bound is exposed to a preparation of antibodies specific for C4 (anti-C4 antibodies) under such conditions as to allow the antibodies to bind to antigenic epitopes present on C4. A number of publicly available antibodies suitable for this purpose may be used. For example, monoclonal antibodies specific for C4 may be obtained commercially from Cytotech, Inc., San Diego, Calif., from Atlantic Laboratories, Scarborough, Me., or as prepared by Dr. Dominic Spinella, Saint Louis Mo. (22). More specific antibodies for detecting isotypes may also be used. These include, for example, anti-C4B monoclonals described by Giles and Ford (8), Giles et. al (9) or O'Neill (23) or those commercially available from Cytotech, San Diego Calif. C4A monoclonals may be prepared as described by Giles, et al., (9) or may be obtained from Dr. John Tamerius at Cytotech. Moreover, although the examples and discussion below relate primarily to detection of C4, in a variation, antibodies against certain other complement components, e.g. C1, could be used to measure levels of those components. Those of ordinary skill in the art should be able to prepare and isolate suitable monoclonal antibodies using techniques more completely described in a number of scientific publications, Spinella (22), Giles and Ford (8), or Kohler and Milstein (24), which are expressly incorporated herein by reference.

While use of monoclonal antibodies in the assay is believed to provide superior results in most cases and is preferred, the assay can also be performed using polyclonal antibodies specific for antigenic epitopes present on the C4d molecule.

After incubation under conditions suitable for the antibody to bind to its respective epitope on the C4 molecule, the amount of antibody bound to the matrix is determined. The relative concentration of C4 present in the test sample can then be quantitated on the basis of the amount of antibody bound, for example, by interpolation from a standard curve.

In some embodiments, it will be advantageous to use an anti-C4 antibody labeled with an enzyme, such as horseradish peroxidase or alkaline phosphatase, capable of cleaving a selected substrate to produce a chromophore. Techniques for enzyme labeling of antibodies and techniques suitable for quantitating the amount of chromophore produced are well known to those in the art of enzyme linked immunoassay and need not be described further here.

Although the present inventor finds the use of enzymatic labels to be the preferred mode of carrying out the assay, other labels, such as radioactive isotopes and fluorochromes can be used in lieu of the enzyme.

It should also be noted that a multi-step or "indirect" labelling procedure may also be used. With those procedures, one first incubates the matrix-bound C4 with a first or primary preparation of anti-C4 antibodies. A secondary reagent that specifically binds the primary reagent is then added. Most commonly, the secondary reagent is an antibody that has specificity for antigenic epitopes present on the primary reagent. However, this is not always the case. For example, where the primary reagent is coupled to biotin, the secondary reagent may comprise avidin.

The secondary reagents may be labeled in the same manner as the primary reagents, e.g., with enzymes, fluorochromes, radioactive isotopes and other known labels.

These and other aspects of the invention will become more readily apparent upon review of the example below. Although the example is intended to illustrate one method of performing the invention, the method of the invention should not be limited by the particulars described below unless specified in the claims.

EXAMPLE I

Test Samples for Study of C4 Levels

Both EDTA plasma and serum frozen and stored at $-70 \sim C$. were obtained from 103 healthy Caucasian volunteers. C4 allotyping was performed by standard methods (4, 17) using carboxypeptidase B and/or neuraminidase type IV (Sigma, St. Louis). Allotype assignment was made on the basis of accepted nomenclature (4).

For further development and standardization of the quantitative C4 immunoassay, samples from a select group of donors with C4 allotypes and three unrelated genetically C4 deficient individuals (25,26) were utilized. Additional studies on those samples included Southern blot analysis of C4 and 21-hydroxylase genes and serological tests for Rodgers and Chido blood group antigens. The C4 cDNA probe (pAT-A) and 21-OHA genomic probe (p21-K4) were kindly provided by Dr. Michael Carroll (Boston Children's Hospital, Boston). Serological tests for Rg1, 2 and Ch 1 through 6 and WH were done by hemagglutination inhibition (27).

Monoclonal Antibodies

Although currently available monoclonal antibodies are not isotype specific, they can be used to quantitate C4A and C4B since they recognize the closely related epitopes Rg and Ch (25). The MoAbs used by the present inventor detect almost all major C4A and C4B allotypes now known.

Monoclonal antibodies were selected for use in the immunoassay here described based on three criteria. First, they had to be specific for C4 as shown by immunoblot analysis. They also had to cause hemagglutination of red cells coated with C4b. Finally, those antibodies showing the highest levels of activity in an ELISA using purified C4 on the microtiter plate were chosen for production as ascites.

The mouse monoclonal antibodies specific for C4d (030II-17.3 and 03II-317.1.3.3) and C4B (057-325.x and 033C-30.27) were obtained from Cytotech, San Diego, Calif. A monoclonal anti-C4A (RGd1) secreting hybridoma was obtained from Tracy Robson (Hammersmith Hospital, London) and injected into Balb/c mice for production of ascites. The MoAbs were purified from ascites by DEAE column chromatography and conjugated to horseradish peroxidase (Behring Diagnostics, La Jolla) using the method of Nakane and Kawoi (28). The MoAbs recognize epitopes present on the activated form of C4, i.e., C4d.

The MoAbs were tested for specificity using serums of selected C4 allotypes including: C4A*Q0,A1,A2,A3-,A4,A5,A6 and B*Q0,B1,B2,B3,B5,B92. The C4A and C4B MoAbs were nonreactive by the immunoassay of the present invention, immunoblot, and serological testing with nine examples each of homozygous C4A*Q0 and C4B*Q0, respectively. Similarly, serum from three total C4-deficient individuals were negative in all three assays (total C4, C4A, C4B).

Immunoassay

In one embodiment, the immunoassay of the present invention was performed as follows. First, human IgG immunoglobulin (Sandoz, East Hanover) was aggregated by heating for 10 minutes at 63 degrees Centigrade. Wells of polystyrene microtiter plates were coated with 100 ug/ml of the heat-aggregated immunoglobulin for 1 hour at $37 \sim C$. and then blocked with 0.5% bovine serum albumin (BSA) prepared in phosphate-buffered saline (PBS).

For testing, sera were diluted 1:50, 1:100 and 1:200 in 0.5% BSA/PBS and 100 ul was added to appropriate wells. The plates were incubated overnight at $4 \sim C$. As a control to ensure that all C4 was bound, sera were then transferred from the first wells into a second set of wells and incubated at $37 \sim C$. for one hour. Following the second incubation, the plates were washed three times with PBS/Tween buffer and 100 ul of diluted monoclonal anti-C4d, C4A or C4B enzyme-conjugate was added. The plates were reincubated at $37 \sim C$. for one hour, washed in PBS/Tween, and 100 ul of o-phenylene-diamine, a chromogenic substrate for horseradish peroxidase, was added. Color development was stopped using 50 ul 4N sulfuric acid and read at 492 nm in a microtiter plate reader (Flow, McClean, Va.) interfaced to a Compaq 386 personal computer.

A standard curve was generated in each plate by diluting reference sera containing only C4A or C4B. Optical density measurements were converted to mg of C4A or C4B by interpolation from the standard curve.

Data was evaluated statistically using the SPSS statistics program (39).

The enzyme linked immunoassay was initially standardized against eight donors of selected C4 allotypes (FIG. 2). Interassay variation using these donors (10 assays of each donor sample) was: 12.4% for total C4, 11.5% for C4A, and 10.8% for C4B. The sensitivity of the assays was approximately 50 ng/ml.

In other studies, sera from each of the 103 normal donors were analyzed for total C4 by both the C4 immunoassay of the present invention and by radial immunodiffusion (RID) (Kallestad, Austin). Hemolytic activity was determined by the CompQuick $Ch_{50}$ test (Sigma, St. Louis). Total serum C4 levels measured by RID were distributed in a normal manner ($X = 30.7 \pm 9.2$) among the adult Caucasian donors. Results obtained using the C4 immunoassay of the present invention correlated well (Pearson's product-moment correlation-coefficient $= 0.81$) with those obtained using the radial immunodiffusion assay. In addition, the sum of individual assays for C4A and C4B correlated well with the C4 immunoassay for total C4 ($R = 0.85$).

Total C4 concentration varied considerably among individuals tested. Consequently, the ranges of C4A and C4B concentrations observed were very also quite broad (FIG. 1). Converting the absolute C4A and C4B values to percentages of total C4 produced a consistent pattern. When a single C4 null gene was present, as determined by allotyping, the percent of C4A or C4B was 35% or less of the total C4. When two null alleles were present in a balanced hemizygous state or when four active genes were present, normal ratios (approximately 50:50) were observed. The levels of C4B in persons with four C4 genes ranged from 50-60% while C4A was 40-50% of the total C4.

Of the 23 donors suspected of having one C4A*Q0 allele as determined by allotyping, 19 were confirmed by the inventor's immunoassay, two gave borderline results, and two showed equal amounts of C4A and C4B. In addition, four samples in which the presence of C4A*00 could not be discerned by allotyping had C4A levels of less than 35% by using the immunoassay of the present invention. These results suggest that those individuals may also be C4A*Q0, and confirm the superiority of the immunoassay of the present invention for diagnosis in certain individuals. Of 20 C4B*Q0 detected by allotyping, 19 were confirmed by the immunoassay of the present invention and one appeared normal. One additional C4B*Q0 was also detected by the immunoassay of the present invention.

The immunoassay described here clearly shows the differences in C4A and C4B levels when a single C4 null gene is present ($p. < .001$). It is interesting to note that the slightly higher levels of C4B than C4A found in individuals with no null genes approaches statistical significance ($p = .059$, $n = 62$). When a single C4A*Q0 is present, only 35% or less of the total C4 is C4A; the opposite is found when C4B*Q0 is present.

The availability of a specific, sensitive, reproducible and accurate assay for the quantitation of C4 gene products offers several advantages. Studies of preferential activation of C4 in vivo, as well as the levels of C4A and C4B in specific autoimmune diseases can now be examined. The assay may also be useful in distinguishing rare or unusual C4 allotypes which may be found in other racial populations.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

REFERENCES

The following references may facilitate understanding or practice of certain aspects of the present invention. Inclusion of a reference in this list is not intended to and does not constitute an admission that such reference represents prior art with respect to the present invention.

1. Swaak AJG, Groenwold J, Bronsveld W: Predictive value of complement profiles and anti-dsDNA in systemic lupus erythemetosus. Annals Rheum Dis 1986; 45:359-66.
2. Guyon JP, Cronstein BN, Morris M., et al.: Serum complement values (C3 and C4) to differentiate between systemic lupus activity and pre-eclampsia. Am J Med 1986; 81:194-200.
3. Yu CY, Campbell RD, Porter RR: A structural model for the location of the Rodgers and the Chido antigenic determinants and their correlation with the human complement component C4A/C4B isotypes. Immunogenetics 1988; 27:399-405.
4. Mauff G, Alper CA, Awdeh ZL, et al: Statement on the nomenclature of human C4 allotypes. Immunobiol 1983; 184-191.
5. Roos MH, Giles CM, Demant P, et al: Rodgers (Rg) and Chido (Ch) determinants on human C4: Characterization of two C4 B5 subtypes, one of which contains Rg and Ch determinants. J Immunol 1984; 133:2634-2640.
6. Rittner C, Giles CM, Roos MH, et al: Genetics of human C4 polymorphism: detection and segregation of rare and duplicated haplotypes. Immunogenetics 1984; 321-333.
7. O'Neill GJ: C4 polymorphism: use of a monoclonal antibody to distinguish C4A and C4B locus products. Vox Sang 1984; 47:362-365.
8. Giles CM, Ford DS: A monoclonal anti-C4d that demonstrates a specificity related to anti-Ch. Transfusion 1986; 26:370-374.
9. Giles CM, Fielder AHL, Lord DK, et al: Two monoclonal anti-C4d reagents react with epitopes closely related to Rg1 and Ch1. Immunogenetics 1987; 26:309-312.
10. O'Neill GJ, Dupont B: Serum C4 levels, Chido, Rodgers, and allotypes of C4 component of complement. Transplant Proc 1979; 11:1102-1105.
11. Olaisen B, Teisberg P, Jonassen R: The C4 system: quantitative studies of different genotypes. Immunobiol 1980; 158:82-85.
12. Uko G, Christiansen FT, Dawkins RL, et al: Reference ranges for serum C4 concentrations in subjects with and without C4 null alleles. J Clin Pathol 1986; 39:573-576.
13. Uko G. Christiansen FT, Dawkins RL: Serum C4 concentrations in the monitoring of systemic lupus erythematosus: requirement for C4 allotyping. Rheumatol Int 1986; 6:111-114.
14. Fielder AHL, Walport MJ, Batchelor JR, et al: Family studies of the major histocompatibility locus in patients with systemic lupus erythematosus: importance of null alleles of C4A and C4B in determining disease susceptibility. Br Med J 1983; 286:425-428.

15. Gaither TA, Alling DW, Frank MM: A new one-step method for the functional assay of the fourth component (C4) of human and guinea pig complement. J Immunol 1974; 13:574-578.
16. Awdeh CL, Raum D, Alper CA: Genetic polymorphism of human C4 and detection of heterozygotes. Nature 1979; 282:205-206.
17. Sim E, Cross SJ: Phenotyping of human complement component C4, a class III HLA-antigen. Biochem J 1986; 230:763-767.
18. Mauff G, Bender K, Giles CM, et al: Human C4 polymorphism: pedigree analysis of qualitative, quantitative and functional parameters as a basis for phenotype interpretations. Hum Genet 1984; 65:362-372.
b 19. Carroll MC, Palsdotirr A, Belt KT, et al: Deletion of complement C4 and 21-hydroxylase genes in the HLA class III region. EMBO J 1985; 4:2547-2552.
20. Yu CY, Campbell RD: Definitive RFLPs to distinguish between the human complement C4A/C4B isotypes and the major Rodgers/Chido determinants: application to the study of C4 null alleles. Immunogenetics 1987; 25:383-390.
21. Holmes E, Cross SJ, Veitch J, et al: Quantitation of human C4A and C4B in serum and plasma by enzyme-linked immunoadsorbent assay. Immunogenetics 1988; 27:295-297.
22. Spinella DG, Shah DD, Hale PD, et al. Monoclonal antibodies to human C4. I. Purification of hemolytically active C4 from small volumes of normal serum. Complement 1984; 1:87-93.
23. O'Neil GJ. C4 polymorphism: use of a monoclonal antibody to distinguish C4A and C4A locus products. Vox Sang 1984; 47:362-65.
24. Kohler G, Milstein C. Continuous cultures of fused cells secreting antibody of predefined specificity. Nature 1975; 256:495-7.
25. Giles CM, Uring-Lambert B, Goetz J, et al: Antigenic determinants expressed by human C4 allotypes; a study of 325 families provides evidence for the structural antigenic model. Immunogenetics 1988; 27:442-448.
26. Ballow M, McLean RH, Einarson, et al: Hereditary C4 deficiency: genetic studies and linkage to HLA. Transplant Proc 1979; 11:1710-1712.
27. Reveille JD, Arnett FC, Wilson RW, et al: Null alleles of the fourth component of complement and HLA haplotypes in familial systemic lupus erythematosus. Immunogenetics 1985; 21:299-311.
28. Nakane PK, Kawoi A: Peroxidase-labeled antibody, a new method of conjugation. J Histochem Cytochem 1974; 22:1084-1091.
29. Norusis MG. The SPSS guide to data analysis. Chicago, SPSS Inc., 1986.
30. Roychouhury AK, Masatoshi N: Human polymorphic genes: world distribution. New York, Oxford Univ Press, 1988, pp. 146-47.
31. Campbell RD, Dodds, AW, Porter RR: The binding of human complement component C4 to antibody-antigen aggregates. Biochem J 1980; 189:67-80.
32. Alcolea JM, Anton LC, Marques G, et al: Formation of covalent complexes between the fourth component of human complement and IgG immune aggregates. Complement 1987; 4:21-32.
33. Paul L. Skanes VM, Mayden J, et al: C4-mediated inhibition of immune precipitation and difference in inhibitory action of genetic variants C4A3 and C4B1. Complement 1988; 5:110-119.
34. Rittner C, Schneider PM: Genetics and polymorphism of the complement components; in Rother K and Till GO (eds): The Complement System. Berlin, Springer-Verlag, 1988, pp. 98.
35. Hughes-Jones NC: The classical pathway. In: Ross GD, ed. Immunobiology of the complement system. Orlando, Academic Press, 1986:21-44.

What is claimed is:
1. An assay method for C4 comprising the steps of:
    a) obtaining a preparation of aggregated immunoglobulin molecules;
    b) affixing said immunoglobulin to a solid matrix;
    c) exposing said immunoglobulin to a sample to be assayed for C4 under such conditions that said C4 will bind to said immunoglobulin; and
    d) exposing said bound C4 to an antibody that specifically binds to C4 under conditions such that binding between C4 and said antibody occurs; and
    e) detecting the antibody bound.
2. An assay method for C4 comprising the steps of:
    a) obtaining a preparation of aggregated immunoglobulin molecules;
    b) affixing said immunoglobulin to a solid matrix;
    c) exposing said immunoglobulin to a sample to be assayed for C4 in the presence of C1 under such conditions that said matrix-bound immunoglobulin will cause capture of C4; and 'd) exposing said captured C4 to an antibody that specifically binds to C4 under conditions such that binding between C4 and said antibody occurs; and
    e) detecting the antibody bound.
3. The method of claim 1 or claim 2 wherein said immunoglobulin comprises IgG.
4. The method of claim 1 or claim 2 wherein said immunoglobulin comprises IgM.
5. The method of claim 1 or claim 2 wherein said antibody is coupled to a labeling molecule and step e) is performed by detecting said label.
6. The method of claim 5 wherein said label is selected from the group consisting of: fluorescent labels and radioactive labels.
7. The method of claim 1 wherein said antibody is coupled to an enzyme capable of cleaving a selected substrate to produce a chromophore and step e) is performed by adding said substrate so that it is cleaved by said enzyme to produce said chromophore and detecting said chromophore.
8. The method of claim 1 wherein said antibody is detected with a secondary reagent capable of specifically binding to said antibody and said secondary reagent is labeled.
9. The method of claim 8 wherein said secondary reagent is an antibody.
10. The method of claim 1 or claim 2 wherein said antibody is a monoclonal antibody specific for a Rodgers antigen.
11. The method of claim 1 or claim 2 wherein said antibody is a monoclonal antibody specific for a chido antigen.
12. An assay method for C4 comprising the steps of:
    a) obtaining a solid matrix having aggregated immunoglobulin affixed thereto;
    b) exposing said immunoglobulin to a sample to be assayed for C4 under such conditions that said C4 will bind to said immunoglobulin; and
    c) exposing said bound C4 to an antibody that specifically binds to C4 under conditions such that binding between C4 and said antibody occurs; and d) detecting the antibody bound.

13. An immunoassay kit adapted for use in a method for detecting C4 in a biological sample by exposing the sample in the presence of C1 to heat-aggregated, ultrasonication-aggregated, or chemically-aggregated immunoglobulin bound to a solid matrix so that C4 becomes affixed to said matrix and is detected by an antibody directed against C4, which kit comprises:
   a) a first container containing the heat-aggregated, ultrasonication-aggregated, or chemically-aggregated immunoglobulin reagent; and
   b) a second container containing the antibody directed against C4;
said aggregated immunoglobulin reagent and antibody being present in a quality and quantity which renders said kit suitable for use in said method.

14. The kit of claim 13 wherein said first container comprises the well of a cell culture dish and said immunoglobulin is bound to said well.

15. The kit of claim 13 further comprising a container comprising a selected concentration of C4.

16. The kit of claim 13 further comprising a container comprising C1.

17. The kit of claim 13 wherein said antibody is labeled with an enzyme capable of cleaving a substrate to produce a chromophore; and said kit further comprises a container comprising said substrate.

18. An immunoassay kit adapted for use in a method for detecting C4 in a biological ample by exposing the sample in the presence of C1 to heat-aggregated, ultrasonication-aggregated, or chemically-aggregated immunoglobulin bound to a solid matrix so that C4 is affixed to said matrix and is detected by an antibody directed against C4, which kit comprises:
   a) a first container containing the heat-aggregated, ultrasonication-aggregated, or chemically-aggregated immunoglobulin reagent; and
   b) a second container containing the antibody directed against C4; and
   c) a third container containing a positive control reagent containing C1 and C4;
aggregated immunoglobulin reagent, antibody, and positive control reagent being present in a quality and quantity which renders said kit suitable for use in said method.

* * * * *

UNITED STATES PATENT AND TRADEMARK OFFICE
CERTIFICATE OF CORRECTION

PATENT NO. : 5,175,083

DATED : December 29, 1992

INVENTOR(S) : Joann M. Moulds

It is certified that error appears in the above-identified patent and that said Letters Patent is hereby corrected as shown below:

On the title page, item (54):

In the Title, insert -- A Novel -- before "Immunoassay".

Column 12:

Column 11, Line 15, delete "b" before "19."

Claim 2, Line 27, delete "(" before "d)" and move "d) exposing said" down to left margin on next line, and then continue the next line thereafter.

Column 11:
Claim 11, Line 58, change "chido" to --Chido--.

Column 14:
Claim 18, Line 6, change "ample" to --sample--.

Claim 18, Line 19, insert -- said -- before "aggregated".

Signed and Sealed this

First Day of February, 1994

Attest:

BRUCE LEHMAN

*Attesting Officer*  *Commissioner of Patents and Trademarks*